United States Patent [19]

Weber

[11] 4,293,310

[45] Oct. 6, 1981

[54] PHOTOELECTROCHEMICAL IMMUNOASSAY

[75] Inventor: Stephen G. Weber, Pittsburgh, Pa.

[73] Assignee: University of Pittsburgh, Pittsburgh, Pa.

[21] Appl. No.: 130,555

[22] Filed: Mar. 14, 1980

[51] Int. Cl.³ .............. G01N 33/54; G01N 27/00; G01N 27/52
[52] U.S. Cl. .............. 23/230 B; 23/915; 204/195 B; 422/68; 424/12
[58] Field of Search .......... 23/230 B, 915; 424/8, 424/12; 204/195 B; 422/68

[56] References Cited

U.S. PATENT DOCUMENTS

| Re. 29,474 | 11/1977 | Axen . | |
|---|---|---|---|
| 3,939,350 | 2/1976 | Kronick . | |
| 3,975,238 | 8/1976 | Bean | 204/195 B |
| 4,005,002 | 1/1977 | Racine | 204/195 B |
| 4,139,348 | 2/1979 | Swartz | 204/195 B |
| 4,150,949 | 4/1979 | Smith . | |
| 4,152,411 | 5/1979 | Schall . | |
| 4,153,675 | 5/1979 | Kleinerman . | |
| 4,160,016 | 7/1979 | Ullman . | |
| 4,160,645 | 7/1979 | Ullman | 23/230 B |
| 4,161,515 | 7/1979 | Ullman . | |
| 4,171,956 | 10/1979 | Uzgiris . | |
| 4,174,384 | 11/1979 | Ullman . | |
| 4,174,952 | 11/1979 | Cannell . | |
| 4,220,450 | 9/1980 | Maggio | 23/230 B |

OTHER PUBLICATIONS

C-T. Lin et al., J.A.C.S., 98:21, 6536-6544, (Oct. 13, 1976).

B. Durham et al., J.A.C.S., communication received Apr. 5, 1978.
S. G. Weber et al., Analytica Chimica Acta, 100, 531-544 (1978).
W. R. Heineman et al., Science, 204, 865 (1979).
J. N. Demas et al., J.A.C.S., 98, 5800-5806, (Sep. 15, 1976).

*Primary Examiner*—Sidney Marantz
*Attorney, Agent, or Firm*—Robert D. Yeager

[57] ABSTRACT

A method and apparatus for the determination of trace amounts of chemicals in a system, as for example the immunoassay determination of hormones, peptides and drugs in biological fluids, applies photoelectrochemistry to the field of immunoassay. The apparatus and method comprise a photoelectrochemically active molecule as a label in an immunoassay system of labeled analyte, antibody sensitive to analyte, quencher and an electrochemical flow cell with light means. The photoelectrochemically active molecule upon photoexcitation transfers an electron to a quencher molecule; the oxidized molecule is subsequently reduced with an electron from an electrode of the flow cell which is held at suitable potential. This electron is measured as photocurrent. The electrochemical flow cell is channeled for the flow of solution containing photoelectrochemically active species and quencher; and has at least one wall transparent to light such as a laser which is trained on the appropriate region of the cell; and further comprises means to isolate the spectral region of interest and means to distinguish photocurrent from nonphotocurrent. The amount of free labeled analyte in the system is determined by the photocurrent signal.

20 Claims, 4 Drawing Figures

PHOTOELECTROCHEMICAL IMMUNOASSAY

BACKGROUND OF THE INVENTION

1. Field of the Invention

This invention relates to the broad field of quantitative chemical analysis and particularly to the field of immunoassay.

2. Description of the Prior Art

IMMUNOASSAY

Immunoassay is an analytical technique by which the concentration of many organic compounds may be determined. The compound for which the concentration is sought is herein referred to as the analyte or species of interest or molecule. Immunoassay has been most widely used in the determination of drugs and hormones in biological fluids. The technique is predicated on the principle that such biochemicals will act as antigens, and thus bind with antibodies to which they are sensitive to form antigen antibody complexes. To describe immunoassay adequately it is first necessary to describe the preparation of the reagents for the analysis. The reagents for any single species (analyte) are unique.

REAGENTS (a) The antibody: The technique requires the presence of a molecule which binds to the species of interest (analyte). This is precisely the mode of action of antibodies, those molecules responsible for the immune response in living organisms. An organism will form antibodies to large foreign molecules. Thus, if a guinea pig is injected with a quantity of human insulin, one may, after a few weeks, obtain from that animal's serum, antibody to human insulin. To form antibodies to small molecules, for example morphine, rather than the larger insulin, one must first create a large molecule which will look to the immune system like the small molecule of interest. Thus to manufacture antibodies to morphine, one must first attach morphine to a carrier molecule and then inject this conjugate into the animal which will manufacture the antibody. A common carrier is the large protein bovine serum albumin (BSA). In this case, the morphine-BSA conjugate is the antigen and morphine is termed the hapten.

(b) The labeled analog to the analyte: The immunoassay is an indirect measurement. Thus one infers the concentration of analyte by measuring the concentration of something else, which in immunoassay is a molecule which looks to the antibody like analyte, but looks to the analyst like a very distinct and easily measurable species (which most biochemical compounds are not). This is done by attaching to a molecule of analyte a species which is easily measurable. Using the aforementioned insulin as an example, insulin may be iodinated with the radioactive $_{125}I$ to create a molecule which is easily detectable by radioactivity measuring devices, yet which maintains sufficient integrity to be recognized by antibody to insulin as a molecule of insulin. Other less commonly used labels have been free-radicals, enzymes, fluorescent labels and electrochemical labels.

TECHNIQUE

At low analyte concentration, where most of the antibody present is not bound to analyte, an increase in the concentration of analyte will result in an increase in the amount bound to antibody. When the antibody has been saturated (i.e., at high concentrations of analyte) there are no more "empty" antibody molecules left for binding, and an increase in concentration of analyte results in no change in the antibody-bound concentration. Thus it is clear that the relationship between antibody-bound analyte (referred to as "bound analyte") and unbound (or free) analyte is a function of analyte concentration.

Immunoassay takes advantage of this fact in the following simple way. A sample containing an unknown concentration of analyte and an excess quantity of antibody is prepared. At equilibrium the ratio of bound analyte concentration to free analyte concentration will be an indicator of the total concentration of analyte present in the sample. These concentrations of bound and free analyte are generally immeasurable, so a tracer is added to the system. The tracer is the labeled analyte. Now the tracer molecule becomes one of the group of analyte molecules, and to determine the bound to free ratio of it will determine the bound to free ratio of analyte, which then may be used to find the total analyte (labeled plus unlabeled) concentration.

The variations in the immunoassay procedure generally occur at two places: (1) the separation of bound analyte from free analyte, and (2) the identity of the label itself. A list of the most common labels has been given, and their mode of action is covered in the following discussion of separation methods. An exhaustive review of labels used is not intended. The separation of bound analyte from free analyte may be performed in three general ways:

(1) Physical separation. This is the earliest and probably most widely used method. The antibodies may be precipitated separating bound (in precipitate) from free (in solution). Alternatively, the free analyte may be removed by adsorption on, for example, dextran coated charcoal, separating bound (in solution) from free (on solid adsorbent). The antibodies may be chemically bound to a solid surface and then one may separate bound (attached to solid surface) from free (in solution).

(2) Chemical separation. By these methods, the molecules are not physically separated, but the differences in their reactivities is used to make the measurement. Two examples will be used. A fluorescent label may be used. A second antibody, this one directed towards the fluorescent label, is used. The fluorescence of the fluorescent label will change when the antibody to the fluorescent label binds to it. However, the antibody to the fluorescent label will not bind to the fluorescence labeled analyte when the fluorescent label is bound to the other antibody (to analyte). The change in fluorescence upon addition of antibody to fluorescent label is thus a measure of how much of the fluorescent labeled analyte is bound to analyte-directed antibody. The second example uses enzyme labeled analyte. Quite simply, the enzymes work, and thus convert some substrate to some measurable product, only when they are not bound to antibody via the analyte molecule. Thus formation of product may be related to amount of analyte bound to antibody.

(3) Kinetic separation. In many cases, the antibody-analyte complex is much larger than the analyte alone. This size difference leads to behavior of the complex occuring on a different time scale than behavior of the analyte alone. Fluorescence depolarization immunoassay is an example of this type of "separation". Light absorption and emission by a molecule occurs along well-defined directions. Thus light which is oscillating in the same plane (plane polarized light) will excite only molecules with a transition moment in the same direction. The opposite holds as well; the polarization of light which is emitted from a population of molecules represents the relative orientations of that population. A mixture of bound and free fluorescent labeled analyte may be excited by plane polarized light. If the molecules were stationary, all the light would be emitted in the same plane. However, molecules are not stationary, and the rate at which they twist around depends on molecular size. Because of the particular sizes and times involved in this experiment, the antibody-bound labeled analyte is relatively stationary and the free labeled analyte rotates a lot. Thus the former will emit light polarized in the same plane as excitation and the latter will emit randomly polarized light. The amount of the fluorescence which remains polarized is thus a function of how much of the label is bound to antibody.

Immunoassays in which the separation is physical are called heterogeneous and those in which the separation is not physical are called homogeneous.

PHOTOELECTROCHEMISTRY

Photoelectrochemistry refers to that branch of electrochemistry in which electron transfer is aided by light. In normal electrochemistry studies one measures properties of systems in which electrons move from a higher energy (perhaps in a chemical species or in an electrode) to a lower energy (again in a chemical species or in an electrode). For instance, silver plating may be accomplished by applying a voltage difference (between a reference electrode and the plating electrode) of sufficient magnitude to raise the electron energy high enough so that it becomes more favorable for the electron to reside on a silver ion than in the electrode. The resulting electron transfer results in the formation of silver metal.

In photoelectrochemistry, the electrons which are transferred are involved with excited state energies. A molecule may absorb a photon increasing the energy of an electron. This electron becomes more reactive since it is at a higher energy, and is, therefore, more easily lost. Some of the energy in the photon may be retained by the chemical system leading to solar energy conversion devices. The field of photoelectrochemistry is being studied for use in energy systems, but has not hitherto found use in analysis.

Radioisotopic immunoassay is extremely useful by virtue of its sensitivity and detectability, however it presents health and environmental hazards. Non radioisotopic immunoassay methods include fluorescence and enzyme immunoassay, which pose fewer hazards, however do not obtain the greater detection ranges possible with radioisotopic immunoassay.

The method and apparatus of the present invention provides the sensitivity and detectability capabilities of radioisotopes without the commensurate problems.

SUMMARY OF THE INVENTION

The apparatus and analytical method of this invention applies photoelectrochemistry to immunoassay to provide a novel technique of immunoassay which eliminates the hazards of radioisotopic immunoassay while still providing the greater detection ranges possible with radioisotopic immunoassay. This method is capable of detecting trace quantities of certain photoelectrochemicals and is herein termed photoelectrochemical immunoasay.

The apparatus and technique of this invention utilizes a photoelectrochemically active molecule as a label in immunoassay, an electrochemical flow cell having an electrode held at suitable potential, and light means. A photoelectrochemically active molecule is herein defined as a molecule which when in solution produces an electrical current at an electrode in response to input of light into the solution. The electrical current produced is herein defined as photocurrent. The photoelectrochemical label of the preferred embodiment is a catalytic light sensitive ruthenium complex, $RuL_3$, wherein L is a derivative of orthophenanthroline or 2,2'-bipyridine. $L_3$ may be a combination of the aforesaid derivatives or 3 molecules of one of the derivatives. Other photoelectrochemically active molecules, such as osmium complex $OsL_3$, may be used within the spirit and scope of the invention.

The photoelectrochemically active label absorbs a photon from the light source or the light means of the apparatus to promote an electron to higher energy. The light means comprise a light source such as a hollow cathode lamp or laser of suitable wavelength. The active label then loses that electron to a suitable quenching species with a vacancy at an energy lower than the excited electron. The active label may also accept an electron from an alternate quenching species. The discussion, but not the scope of the invention, will be limited to the oxidative quenching. A quenching species, also termed a quencher molecule or quencher is herein defined as a molecule which removes an excited molecule from its excited state by electron transfer. A monochromator, light beam chopper, filters and lenses are included in the light means to control the quenching reaction. The aforesaid electrode of suitable potential may then donate an electron to the oxidized label, $RuL_3^{3+}$, returning it to the ground state in reduced form, $RuL_3^{2+}$ from where it began. This cycle may be repeated ad infinitum in the presence of sufficient quenching species such as $Co(C_2O_4)^{3-}$ or hydrazine; the electron donated from the electrode is measured as photocurrent.

In photoelectrochemical immumoassay the concentration of analyte is determined by making a measurement of the photoelectrochemically labeled analyte. Any molecule to which an antibody may be formed may be used as an analyte.

The photoelectrochemical method and apparatus of immunoassay essentially comprises (i) a photoelectrochemically labeled analyte and quencher in an essay and (ii) measuring the photocurrent of said labeled analyte in apparatus comprising, a photoelectrochemical cell having at least one wall transparent to light of the appropriate spectrum for excitation; light means comprising a light source such as laser or hollow cathode lamp, and means for isolating said appropriate spectrum and distinguishing photocurrent and nonphotocurrent.

DETAILED DESCRIPTION OF THE PREFERRED EMBODIMENT

The unique feature of photoelectrochemical immunoassay is its high selectivity and sensitivity as an analytical tool. Selectivity refers to the cleanliness of the system response. A system which responds to many compounds as it does to the analyte is not selective. The photoelectrochemical system is much more selective than standard voltammetric systems due to the added parameter-light intensity. An electrochemical current which does not vary with the light intensity cannot be photoelectrochemical in nature and, therefore, should be ignored. By appropriate experimental design, only photoelectrochemical current is measured.

Sensitivity refers to the net system response due to a given number or concentration of analyte molecules. Since the particular photoelectrochemical species of the present invention is involved in a catalytic cycle, one analyte molecule may contribute more than one equivalent of current and, therefore, sensitivity is higher than non-catalytic voltammetric detection.

The components of the photoelectrochemical immunoassay technique and method of this invention include an electrochemical flow cell, light means, photoelectrochemically labeled analyte, and antibody sensitive to analyte. Because photoelectrochemical immunoassay involves the application of photoelectrochemistry to the field of immunoassay, it will be helpful to detail the mechanism of the electron transfer quenching of the photoelectrochemically active molecule.

PHOTOELECTROCHEMISTRY OF $RuL_3$

Figure 1:
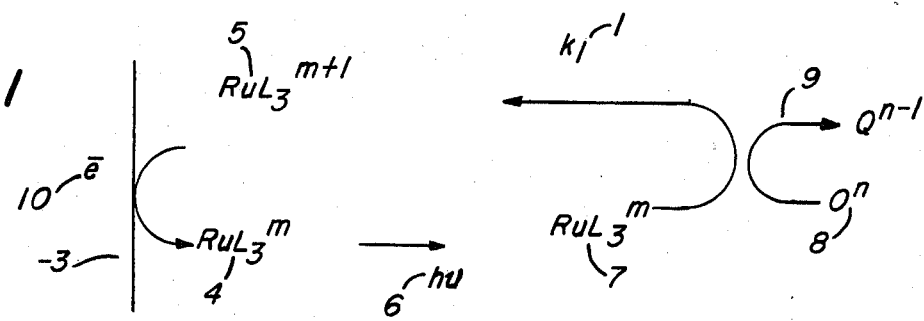
FIG. 1 is a diagram of the photoelectrochemical mechanism of the ruthenium complex in electron transfer quenching in solution.

When a solute molecule becomes photoexcited and an electron transfer occurs in a solution, this is an electron transfer quenching of a photoexcited state. A molecule of $RuL_3$ is susceptible to photoexcitation and electron transfer quenching. The mechanism (1) for this reaction is shown in FIG. 1. Ru is ruthenium, L is ligand, m is the valence state for the ruthenium complex, $RuL_3$, Q is the quencher species, and n is the valence state of the quencher species, e is the electron. If the electrode 3 is at a potential between 1.015 V and +1.52 V, vs. saturated calomel electrode, $RuL_3{}^{2+}$ (for L=2,2' bipyridine) will not undergo a charge transfer reaction with the electrode 3. The above potentials correspond to $E°_{RuL_3{}^{3+/2+}}$ and $E°_{RuL_3{}^{2+/1+}}$, respectively. In the presence of light 6, however, the following occurs. $RuL_3{}^m$ 4 is photoexcited to $RuL_3{}^{m*}$ 7 and is quenched by a molecule of quencher, $Q^n$ 8 by transfer of an electron from $RuL_3{}^{m*}$ 7 to $Q^n$ 8 to form $RuL_3{}^{m+1}$ 5 and $Q^{n-1}$ 9. This results in a molecule of $RuL_3{}^{m+1}$ 5 able to accept an electron 10 from the electrode 3. In undergoing the electron transfer the original molecule of $RuL_3{}^m$ 4 is produced. This entire process may be repeated and each time an electron transfer event occurs, a measurable electron flow (current) is produced. In the presence of light the overall effect is that the electrode reduces the quencher by way of the photocatalysis of $RuL_3{}^m$. Thus it is shown in the reaction mechanism of the quenching of a photoelectrochemical molecule, that essential elements of the system also include a suitable quenching species, light source and electrode. Therefore these elements will be set forth in greater detail below.

QUENCHERS

A quencher as defined for purposes of this invention is a molecule which removes an excited molecule from its excited state by electron transfer. The use of a proper quencher is extremely important in this system, since the most serious chemical interference would be one in which non-productive quenching of $RuL_3$ occurred. This could be an energy transfer quenching, during which $$RuL_3{}^{m*} + Q^n \rightarrow RuL_3{}^m + Q^{n*}; \quad \text{(Equation 1)}$$

or it could be an electron transfer quenching with a rapid back reaction:

$$RuL_3{}^{m*} + Q^n \rightarrow RuL_3{}^{m+1} + Q^{n-1}; \text{ and} \quad \text{(Equation 2)}$$

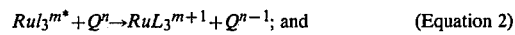

$$RuL_3{}^{m+1} + Q^{n-1} \rightarrow RuL_3{}^m + Q^n. \quad \text{(Equation 3)}$$

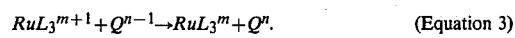

The preferred quencher of the method of this invention is $Co(C_2O_4)_3{}^{3-}$. Some quenchers, in their reduced form, $Q^{n-1}$, tend to react with the $RuL_3{}^{m+1}$ formed during the quenching process Equation 3. The products of this reaction are $Q^n$ and $RuL_3{}^m$, and there is thus no molecule to react at the electrode to give signal current. However quenching by the molecule $Co(C_2O_4)_3{}^{3-}$ yields $RuL_3{}^{m+1}$ and aquated $Co^{2+}$. The ruthenium complex, $RuL_3{}^{m+1}$, will then react with the electrode. This quencher, however, works only in acid solutions and thus requires separation of bound analyte from free analyte before making the photoelectrochemical measurement. The preferred use of this quencher in a photoelectrochemical assay is therefore in a heterogeneous assay where only the free analyte is injected into the apparatus to obtain the photoelectrochemical measurement.

In order to perform the immunoassay homogeneously, a photoelectrochemical measurement must be made at near neutral conditions to preserve the integrity of the antibody. Again it is important that the quencher does not undergo a rapid back reaction with the ruthenium complex, $RuL_3{}^m$; therefore a molecule of quencher which breaks apart upon one electron reduction is necessary to prevent back reaction. Hydrazine, which requires two electrons for reduction to a water-stable species ($2NH_3$) and is a mild oxidant (which is cleaved on reduction), is effective in pH 7.0 phosphate buffered solution. This yields a photoelectrochemical signal which is 10% of the signal from $Co(C_2O_4)_3{}^{3-}$ in 1 M acid. Thus, buffered hydrazine will provide a suitable quencher for homogeneous immunoassay. Other suitable quenchers capable of oxidizing or reducing a photoelectrochemical molecule in this manner without undergoing a rapid back reaction, may be used within the spirit and scope of this invention.

Electrochemical Flow Cell With Light Means

A flow through electrochemical cell with a standard set of electrodes is utilized. The electrodes include (i) working electrodes where the electron transfer of interest occurs which are preferably constructed of gold, platinum or carbon for oxidation, (ii) an auxilliary electrode of stainless steel or platinum which completes the electrical circuit with the working electrode by carrying an equal and opposite current to that of the working electrode and (iii) a reference electrode which maintains a constant potential and to which the working electrode is set in relation. The cell further comprises standard controlling electronics (potentiostat); a constant flow rate pump such as that which is common in high performance liquid chromatography, with a stream of pump fluid flowing through a polytetrafluorethylene tube into the electrochemical cell, and an injection device between the pump and the cell. A solution of quenching compound is continually pumped into the cell by this means.

The bound and free analyte are both present during the measurement in a homogeneous assay. In order to accurately measure the free labeled analyte in the presence of bound labeled analyte it is necessary to make a measurement that is rapid with respect to the time required for a molecule of bound labeled analyte to disassociate into a molecule of free labeled analyte and a molecule of antibody. Otherwise during the course of the measurement of molecules of free labeled analyte which have disassociated from the bound state will be measured, resulting in erroneous measurement. The dimensions of the cell are critical in determining the percent error to be expected in the immunoassay measurement. Calculations have been worked out for these cell dimensions, (where the cell takes the shape of the channel electrode), in the *Behavior Of An Electrochemical Detector Used In Liquid Chromatography In Continuous Flow Voltammetry* by Stephen G. Weber and William C. Purdy, *Analytica Chemica Acta*, 100, pp. 531–544, (1978), which is herein incorporated by reference. The dimensions of the cell (wherein A in $cm^2$ = area of electrode and b = thickness of the spacer in cm); the diffusion coefficient of the labeled analyte (D $cm^2 s^{-1}$); and the flow rate of the stream running through the cell ($\overline{U}$ $cm^3 s^{-1}$), may be combined into a characteristic dimensionless parameter called r.

$$r = AD/\overline{U}b \quad \text{(Equation 4)}$$

Figure 2:
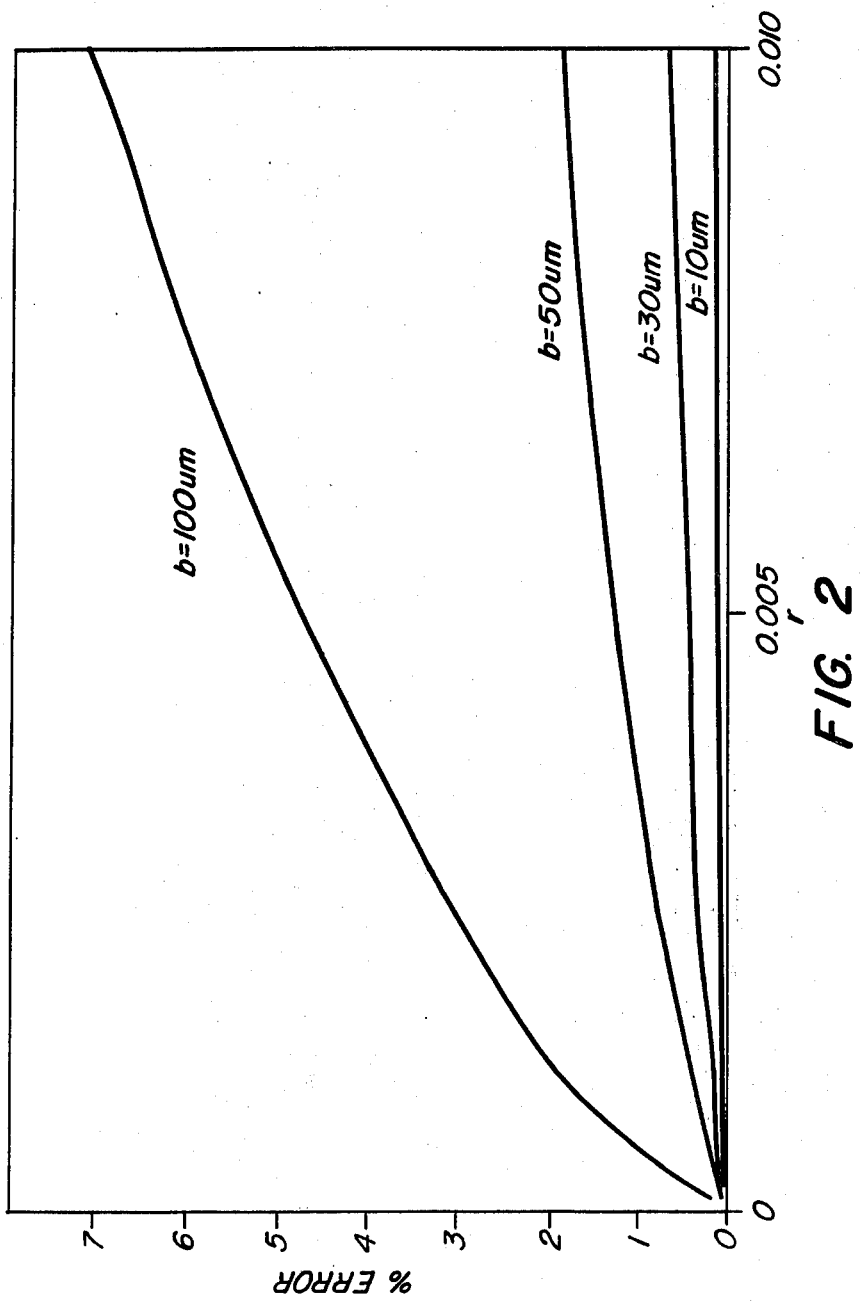
FIG. 2 is a graph diagramming percent error of the photoelectrochemical method of immunoassay as a function of r, where $r = AD/Ub$.

FIG. 2 shows the percent error as a function of r, with the teflon spacer thickness, b, as a parameter. This figure has been calculated on the basis of an antibody-ligand dissociation rate constant of $1s^{-1}$. This is a large rate constant, and so the indicated percent error may be taken as an upper limit. One may use this figure to establish satisfactory homogeneous assay conditions. For instance, at the level of 0.5% error, one may use r = 0.008, and b = 30 μm. For a typical molecule, D = $5 \times 10^{-6} cm^2 s^{-1}$ as a good approximation, thus $8 \times 10^{-3} < A(cm^2)/\overline{U}(cm^3 min^{-1})$. Conditions are then easily set.

The cell must have at least one wall which is transparent to light that is of a wavelength which will excite the photoelectrochemically active species. The source of light may be: (i) laser, suitable for the ruthenium species described herein, such as argon ion laser or dye laser, which has a wavelength range of interest of 430–500 nm., (ii) a hollow cathode lamp, such as a strontium lamp with its strong line at 460.7 nm., or (iii) a Xe or Xe-Hg arc lamp. A monochromater is required to isolate the spectral region of interest.

The light must be trained on the appropriate region of the cell in appropriate form and a means of discriminating between electrochemical signals which are caused by the light and signals not caused by the light must be provided. These two elements are discussed in greater detail below with reference to FIG. 3 showing a preferred embodiment of the electrochemical flow cell and light means, and FIG. 4 showing an alternate embodiment of the electrochemical flow cell and light means.

The relative orientation of the plane of the electrodes in exciting light may take essentially two alternative forms.

Figure 3:
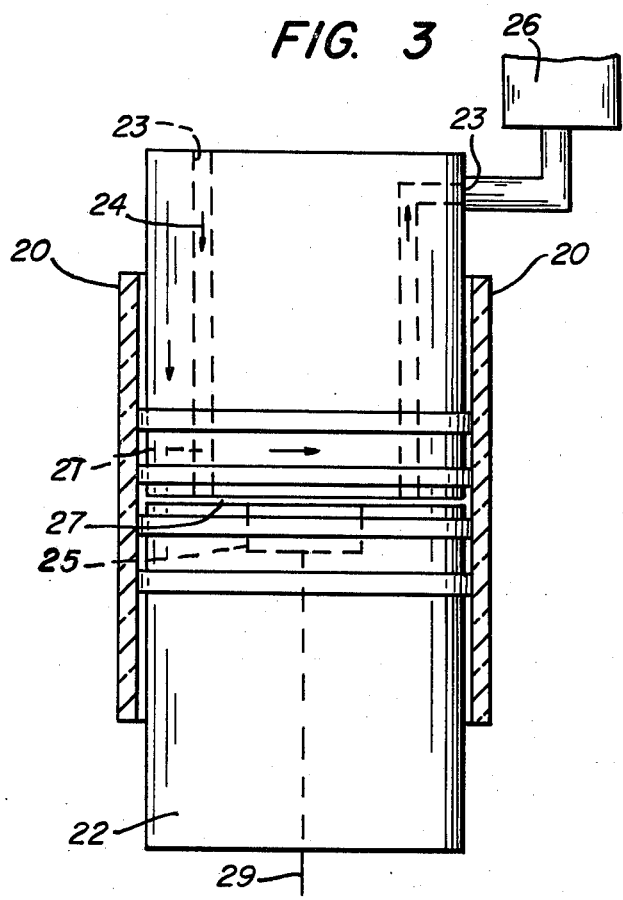
FIG. 3 is a schematic diagram of a flow cell of the preferred embodiment.

In the preferred embodiment of the flow cell 20 of the present invention as shown schematically in FIG. 3, the light is directed across the plane of the working electrode/solution interface. The light here has been made into a ribbon-like beam to fit into the small channel space 27 created by the teflon spacer ordinarily used (10–50 μm). The channel 27 is continuous through the cell body 22, opening to the exterior of openings 23 and the reacting solution 24 is thereby continuously pumped through the cell. In this embodiment, the auxiliary and reference electrodes are in chamber 26. This method of directing the light provides greater density of light in front of the working electrode 25 and yields to higher sensitivity in the results. In order to discriminate between electrochemical signal caused by light and signal not caused by light in the preferred embodiment the light is interrupted at regular intervals ~1 Hz (or modulated), and the resulting modulated signal may be detected with a lock-in amplifier (not shown). This method of measurement, termed synchronous detection, is preferred for quenching systems, such as the system of the present invention, which respond rapidly to a light pulse.

Figure 4:
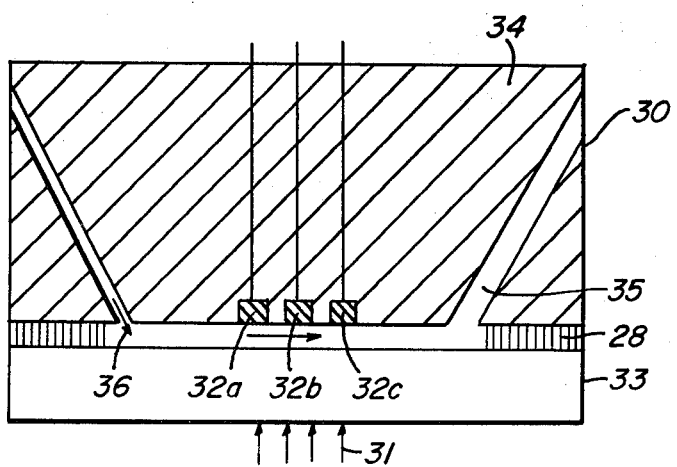
FIG. 4 is a schematic diagram of a flow cell of an alternate embodiment.

In the alternate embodiment of cell 30 as shown in FIG. 4, the light 31 may impinge perpendicularly to the face of the electrodes 32. In this case, the wall 33 of the cell opposite to electrodes 32 is made of glass. Teflon spacer 28 inserted between glass wall 33 and the solid cell body 34 forms channel 35 holding solution 36. A beam of light 31 enters the cell 30, striking solution 36 in front of the electrodes 32 initiating the photoelectrochemical reaction. Three identical carbon electrodes, 32a, 32b and 32c, are shown in cell 30. The means of discriminating between electrochemical signal caused by light and signal not caused by light in the alternate embodiment may be one of two forms.

One of the electrodes is used as an auxiliary electrode, one is a working electrode kept in the dark and one is a working electrode in the light. The difference in the current signals of the latter two electrodes is taken as the signal due to the presence of light. Alternatively, synchronous detection is also used in this embodiment as a means of discriminating between photoelectrochemical signals and nonphotoelectrochemical signals and thus a modulated light source resulting in a modulated signal can be detected with a lock-in amplifier which is again provided.

Preparation of Ruthenium Complex Labeled Analyte

Because the photoelectrochemical molecule is used in immunoassay it is necessary for the molecule to be coupled with the analyte of interest to provide labeled analyte. Thus it will be useful to describe in some detail a method of preparation of a photoelectrochemically active molecule such as tris (2,2'-bipyridyl) ruthenium (II).

The synthesis of labeled analyte may be done by isothiocyanate route.

Antibodies are commercially available and can be purchased; analytes which are amines may be labeled as follows (for example, proteins, peptids, amphetamins and other drugs):

(A) Preparation of 4,4'-diiosothiocyanato-2,2'-bipyridyne (I).

(1) Prepare 4,4'-dicarboxyl-2,2'-bipyridyne (II). P. J. Delaire, J. T. Lee, H. Abruña, H. W. Sprintschnik, T. J. Meyer and D. G. Whitten, in *Inorganic and Organometallic Photochemistry*, Ed. M. S. Wrighton, American Chemical Society, p. 28, (1978). G. H. W. Sprintschnik, P. P. Kirsch and D. G. Whitten, J. Am. Chem. Soc. 99, 4947 (1977).

(2) 4,4'-diisothiocyanato-2,2'-bipyridyne is synthesized by the Hofmann rearrangement [E. Magnien and R. Baltzly, J. Org. Chem. 23, 2029 (1958)] of II to the amine and reaction with $CS_2$ and $Pb(NO_3)_2$ to the isothiocyanate (I). S. R. Sandler and W. Karo, *Organic Functional Group Preparation*, Ed., A. T. Blomquist, Academic Press, New York (1968), p. 312.

(B) Prepare the 4,4'-diisothiocyanato-2,2'-bipyridyl- bis (2,2'-bipyridyl) ruthenium (II). F. H. Burstell, J. Chem. Soc. 173 (1936).

(C) Prepare the labeled analyte. S. Udenfriend, *Fluorescence Assay in Biology and Medicine*, Eds., N. O. Kaplan and H. A. Scheraga, Academic Press, New York (1962), p. 221. Other analytes of interest (hydroxy containing species) may be labeled using 4,4' dicarboxy 2,2' bipyridine.

OPERATIONAL EXAMPLE

The detecting apparatus of the present invention comprises: (i) catalytic photoelectrochemical label such as the ruthenium complex, which is capable of generating a photocurrent at an electrode held at appropriate potential, (ii) a quencher such as $Co(C_2O_4)_3^{3-}$, or hydrazine and (iii) an electrochemical flow cell with light means which controls the electrochemical reactions of the system, said cell having at least one wall which is transparent to light of a wave length which will excite the photoelectrochemically active species, and said light means includes a light source such as a laser or hollow cathode lamp, and monochromater, filter and/or lenses as necessary to isolate the required spectral region, and means to distinguish photocurrent and non-photocurrent such as a light beam chopper; wherein said cell and light means are oriented such that light is focused on the appropriate region of the cell in the appropriate form as for example, a perpendicular or parallel impingement.

The method of catalytic photoelectrochemical immunoassay comprises the steps of (i) utilizing a photoelectrochemical label, such as a ruthenium complex, to form a labeled analyte; and a quencher molecule which is capable of removing an excited molecule from its excited state by electron transfer, in an immunoassay system; and (ii) measuring a concentration of said photoelectrochemically labeled analyte in an electrochemical flow cell having at least one transparent wall and including a light source, such as laser or hollow cathode lamp the light from which is capable of penetrating said transparent wall and exciting the photoelectrochemically active species; means to isolate the spectral region of interest, such as a monochromater; and means to distinguish between a photocurrent and non-photocurrent.

In operation the method and apparatus is applied as follows: A heterogeneous analysis for morphine is used as an example. The antibody is purchased or prepared using standard methods. The labeled analyte may be prepared from the 4,4' dicarboxy 2,2' bipyridyl bis (2,2'-bipyridine) ruthenium and morphine to form the 3-0-morphinyl ester. The antibody containing serum is titrated with labeled analyte to determine that concentration of antibody which will give a bound to free ratio near 1, for low concentrations of analyte. Standards are prepared from aqueous solutions of morphine sulfate.

(1) Antibody are labeled antigen solutions are mixed in the proper proportion to give a bound to free ration of 1 as determined earlier. (Total volume 500 uL)

(2) Sample containing morphine (volume 100 uL), e.g.
  (a) blood serum
  (b) urine (centrifuged and decanted to remove precipitate)
  (c) aqueous solution of morphine prepared from
    (i) aqueous standards
    (ii) dissolving a residue resulting from extraction of biological fluid or medication is added to the mixture made in step 1 and the system is allowed to equilibrate for fifteen minutes at room temperature.

(3) A protein precipitating agent, $(NH_4)_2SO_4$ 3 M (volume 1 mL) is added and after ten minutes the suspension is centrifuged to remove protein.

(4) The supernatant from this is mixed with an equal volume of 2 M $H_3PO_4$, $2 \times 10^{-2}$M $K_3Co(C_2O_4)_3$. This mixture is injected, using a standard loop injector, into a solution flowing through the cell in its preferred embodiment. The solution which carries the plug of injected sample to the cell is 1 M $H_3PO_4$, $10^{-2}$M $K_3Co(C_2O_4)_3$.

(5) The photoelectrochemical signal is plotted vs. the concentration of morphine for various concentrations of aqueous standards to give a standard curve.

(6) The concentration of morphine from any unknown may be determined by reference to the standard curve.

The photoelectrochemistry of this system is controlled by conditions of the electrochemical flow cell and light means. Because the label is photo-sensitive, current generated by the photoelectrochemical reaction is distinguishable from any current generated by other chemical species and/or reactions (for example, unlabeled analyte or other reagent molecules), by methods such as synchronous detection. Furthermore, when homogeneous assay is used the antibody-bound photoelectrochemically active species do not react at the electrode surface, while with the use of a suitable quencher, such as hydrazine, the free photoelectrochemically active species will be able to react at the electrode surface. Therefore, only free labeled analyte is measured and, due to the catalytic properties, it is measured at extremely low concentrations.

What is claimed is:

1. Immunoassay apparatus comprising:
   (i) a catalytic photoelectrochemical label capable of photoexcitation such that a photocurrent is generated at an electrode of appropriate potential;
   (ii) a quencher; and
   (iii) an electrochemical flow cell having,
     at least one wall transparent to light of a spectrum which will excite said photoelectrochemically active label, and
   (iv) light means which further comprise,
     a light source having a spectrum capable of exciting said photoelectrochemically active label, and means for isolating said spectrum, wherein the relative planes of orientation of the electrodes of said cell, and said spectrum are disposed such that said photoelectrochemically active label will react with said quencher to generate said photocurrent, and means for distinguishing between said photocurrent and non-photocurrent.

2. The detecting apparatus of claim 1 wherein said photoelectrochemically active label is a ruthenium complex.

3. The detecting apparatus of claim 2 wherein said ruthenium complex is $RuL_3$ and L is a derivative of o-phenanthroline or 2,2'-bipyridine or combination thereof.

4. The detecting apparatus of claim 3 wherein said $RuL_3$ is tris (2,2'-bipyridyl) ruthenium (ii).

5. The detecting apparatus of claim 1 wherein said photoelectrochemically active label is an osmium complex.

6. The detecting apparatus of claim 5 wherein said osmium complex is $OsL_3$ and $L_3$ is a derivative of o-phenanthroline or 2,2'-bipyridine or combinations thereof.

7. The detecting apparatus of claim 1 wherein said quencher is $Co(C_2O_4)_3^{3-}$.

8. The detecting apparatus of claim 1 wherein said quencher is hydrazine.

9. The detecting apparatus of claim 1 wherein said light source is a hollow cathode lamp.

10. The detecting apparatus of claim 9 wherein said cathode is a strontium lamp.

11. The detecting apparatus of claim 1 wherein said light source is a Xe arc lamp.

12. The detecting apparatus of claim 1 wherein said light source is a laser.

13. The detecting apparatus of claim 1 wherein said means for distinguishing between said photocurrent and non-photocurrent further comprises a light beam chopper, filters, lenses and lock-in amplifier.

14. The detecting apparatus of claim 1 wherein said means for distinguishing between said photocurrent and non-photocurrent further comprises a first working electrode exposed to said light and a second working electrode in the dark, such that the difference in current signals is the signal due to the presence of light.

15. The detecting apparatus of claim 1 wherein said isolated spectrum is in one range at 430-500 nm.

16. The detecting apparatus of claim 14 wherein said means for isolating said spectrum further comprises a monochromater.

17. The detecting apparatus of claim 1 wherein said relative planes of orientation are disposed such that said spectrum impinges perpendicularly to said electrodes.

18. The detecting apparatus of claim 1 wherein said relative planes of orientation are such that said spectrum impinges parallel to said electrodes.

19. A catalytic photoelectrochemical method of immunoassay comprising the steps of:
(i) utilizing a photoelectrochemically labeled antigen and quencher in an assay of analyte, labeled analyte and antibody specific to said analyte, and
(ii) measuring the concentration of said photoelectrochemically labeled analyte with an electrochemical flow cell, having means for distinguishing photocurrent and non-photocurrent; light means which further comprises a light source, having a spectrum capable of exciting said photoelectrochemically active label, and means for isolating said spectrum, wherein the relative planes of orientation of the electrodes of said cell, and said spectrum are disposed such that said photoelectrochemically active label will react with said quencher to generate said photocurrent.

20. A catalytic photochemical method of immunoassay comprising the steps of:
(i) utilizing a photoelectrochemical as a label with a labeled analyte, and a quencher, in an assay mixture of analyte, labeled analyte and antibodies specific to said analyte, and
(ii) measuring the concentration of said photoelectrochemically labeled analyte with an electrochemical flow cell, having,
at least one wall transparent to light of a spectrum which will excite said photoelectrochemically active label, means for distinguishing between said photocurrent and nonphotocurrent and
light means which further comprises,
a light source having a spectrum capable of exciting said photoelectrochemically active label, and means for isolating said spectrum, wherein the relative planes of orientation of the electrodes of said cell, as a spectrum are disposed such that said photoelectrochemically active label will react with said quencher to generate said photocurrent.

* * * * *

UNITED STATES PATENT AND TRADEMARK OFFICE
CERTIFICATE OF CORRECTION

PATENT NO. : 4,293,310

DATED : October 6, 1981

INVENTOR(S) : Stephen G. Weber

It is certified that error appears in the above—identified patent and that said Letters Patent is hereby corrected as shown below:

Col. 1, line 56, delete "$125^I$" and substitute therefor
--$^{125}I$--;

Col. 4, line 51, delete "essay" and substitute therefor
--assay--;

Col. 4, line 66, delete "AD/Ub" and substitute therefor
--$\dfrac{\underline{AD}}{\overline{Ub}}$--;

Col. 5, line 55, delete "$Q^{n-9.}$" and substitute therefor
--$Q^{n-1}9.$--;

Col. 6, line 16, delete "Rul" and substitute therefor
--RuL--;

UNITED STATES PATENT AND TRADEMARK OFFICE
CERTIFICATE OF CORRECTION

PATENT NO. : 4,293,310  Page 2 of 2
DATED : October 6, 1981
INVENTOR(S) : Stephen G. Weber It is certified that error appears in the above—identified patent and that said Letters Patent is hereby corrected as shown below:

Col. 7, line 37, delete "AD/Ub" and substitute therefor

-- $\dfrac{AD}{\overline{Ub}}$ --; and

Col. 10, line 4, delete the first occurrence of the word "are" and substitute therefor --and--.

Signed and Sealed this

Nineteenth Day of January 1982

[SEAL]

Attest:

GERALD J. MOSSINGHOFF

Attesting Officer    Commissioner of Patents and Trademarks